US012648708B2

(12) United States Patent
Maki et al.

(10) Patent No.: US 12,648,708 B2
(45) Date of Patent: Jun. 9, 2026

(54) MOUNTING TOOL, MEASUREMENT SYSTEM, AND DETERMINATION METHOD

(71) Applicant: TERUMO KABUSHIKI KAISHA, Tokyo (JP)

(72) Inventors: Shin Maki, Ebina (JP); Tomoko Uemura, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 675 days.

(21) Appl. No.: 17/487,604

(22) Filed: Sep. 28, 2021

(65) Prior Publication Data

US 2022/0007960 A1    Jan. 13, 2022

Related U.S. Application Data

(63) Continuation of application No. PCT/JP2020/013129, filed on Mar. 24, 2020.

(30) Foreign Application Priority Data

Mar. 29, 2019    (JP) .................................. 2019-066652

(51) Int. Cl.
    *A61B 5/0537* (2021.01)
    *A61B 5/00* (2006.01)
    (Continued)

(52) U.S. Cl.
    CPC .......... *A61B 5/0537* (2013.01); *A61B 5/0004* (2013.01); *A61B 5/251* (2021.01);
    (Continued)

(58) Field of Classification Search
    CPC ... A61B 5/0537; A61B 5/0004; A61B 5/6805; A61B 5/25; A61B 5/254; A61B 5/256;
    (Continued)

(56) References Cited

U.S. PATENT DOCUMENTS

| | | | |
|---|---|---|---|
| 5,782,238 A | 7/1998 | Beitler | |
| 2002/0004992 A1* | 1/2002 | Oser ...................... | A61B 5/107 33/555.4 |

(Continued)

FOREIGN PATENT DOCUMENTS

| | | |
|---|---|---|
| CN | 1426287 A | 6/2003 |
| CN | 1492744 A | 4/2004 |

(Continued)

OTHER PUBLICATIONS

International Search Report (PCT/ISA/210) with translation and Written Opinion (PCT/ISA/237) mailed on Jun. 16, 2020, by the Japanese Patent Office as the International Searching Authority for International Application No. PCT/JP2020/013129.

(Continued)

*Primary Examiner* — Jason M Sims
*Assistant Examiner* — Kyle W. Kretzer
(74) *Attorney, Agent, or Firm* — BUCHANAN INGERSOLL & ROONEY PC

(57) ABSTRACT

Provided is a mounting tool that is capable of executing measurement processing of impedance of a living body by applying a current to the living body and that is capable of being mounted on a user, the mounting tool including: three or more electrodes; a body shape estimation unit configured to estimate a body shape of the user mounted with the mounting tool; and a control unit configured to determine a combination of electrodes to be used for measuring the impedance of the living body among the three or more electrodes based on the body shape of the user estimated by the body shape estimation unit.

12 Claims, 7 Drawing Sheets

(51) Int. Cl.
    *A61B 5/251*     (2021.01)
    *A61B 5/256*     (2021.01)
    *A61B 5/279*     (2021.01)

(52) U.S. Cl.
    CPC .............. *A61B 5/256* (2021.01); *A61B 5/279*
                (2021.01); *A61B 5/6843* (2013.01)

(58) Field of Classification Search
    CPC ....... A61B 5/257; A61B 5/251; A61B 5/6843;
                A61B 5/107; A61B 5/1072; A61B 5/1077
    See application file for complete search history.

(56) References Cited

U.S. PATENT DOCUMENTS

| | | | |
|---|---|---|---|
| 2003/0187363 A1 | 10/2003 | Alroy | |
| 2004/0077969 A1 | 4/2004 | Onda et al. | |
| 2005/0101883 A1* | 5/2005 | Santos ................... | A61B 90/06 |
| | | | 600/587 |
| 2008/0064964 A1 | 3/2008 | Nagata et al. | |
| 2010/0121216 A1* | 5/2010 | Hamaguchi .......... | A61B 5/0537 |
| | | | 600/547 |
| 2012/0172747 A1* | 7/2012 | Fukuda ................. | A61B 5/107 |
| | | | 600/547 |
| 2013/0190588 A1 | 7/2013 | Karo et al. | |
| 2017/0086699 A1* | 3/2017 | Shirai ................... | A61B 5/282 |
| 2017/0086742 A1* | 3/2017 | Harrison-Noonan ........................ | |
| | | | A61B 5/6843 |

FOREIGN PATENT DOCUMENTS

| | | |
|---|---|---|
| CN | 102961135 A | 3/2013 |
| JP | 2001218748 A | 8/2001 |
| JP | 2002291912 A | 10/2002 |
| JP | 2007068777 A | 3/2007 |
| JP | 2018121818 A | 8/2018 |
| WO | 2005089645 A1 | 9/2005 |
| WO | 2012023340 A1 | 2/2012 |

OTHER PUBLICATIONS

English Translations of the International Search Report (Form PCT/ISA/210) and the Written Opinion of the International Searching Authority (Form PCT/ISA/237) issued Jun. 16, 2020, by the Japan Patent Office in corresponding International Application No. PCT/JP2020/013129. (8 pages).

The First Office Action issued on Apr. 10, 2025, by the China National Intellectual Property Administration in corresponding Chinese Patent Application No. 202080024346.9 and English translation of the Office Action. (13 pages).

* cited by examiner

Figure 6:
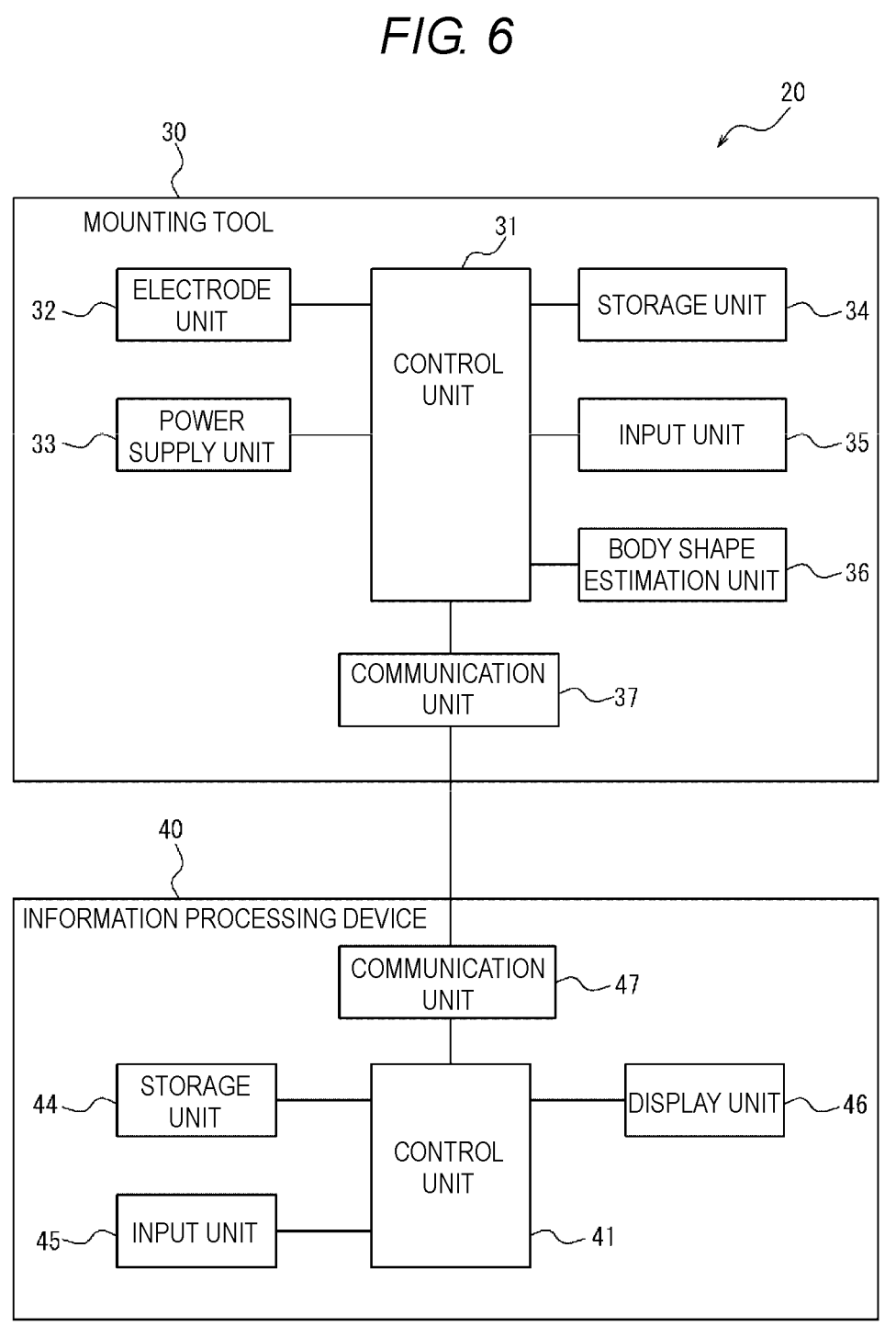

MOUNTING TOOL

31

32 — ELECTRODE UNIT

33 — POWER SUPPLY UNIT

CONTROL UNIT

STORAGE UNIT — 34

INPUT UNIT — 35

BODY SHAPE ESTIMATION UNIT — 36

COMMUNICATION UNIT — 37

40

INFORMATION PROCESSING DEVICE

COMMUNICATION UNIT — 47

44 — STORAGE UNIT

45 — INPUT UNIT

CONTROL UNIT

DISPLAY UNIT — 46

— 41

MOUNTING TOOL, MEASUREMENT SYSTEM, AND DETERMINATION METHOD

CROSS-REFERENCES TO RELATED APPLICATIONS

This application is a continuation of International Application No. PCT/JP2020/013129 filed on Mar. 24, 2020, and claims the benefit of Japanese Application No. 2019-066652 filed on Mar. 29, 2019, the entire content of each of which is incorporated herein by reference.

FIELD OF THE INVENTION

The present disclosure relates to a mounting tool, a measurement system, and a determination method.

BACKGROUND DISCUSSION

Devices for measuring moisture contained in a living body by causing current to flow therethrough to measure its impedance are known in the related art. For example, JP-A-2001-218748 discloses a pulmonary water amount display device that measures and displays a moisture amount of a lung using such a bioelectrical impedance method.

In order to cause current to flow through the living body using such a device, it is known to connect, i.e., bring into contact, an electrode with the living body. However, a penetration depth of the current applied to the living body varies depending on a connection position of the electrode to the living body. Therefore, depending on the connection position of the electrode to the living body, the current may not reach a position where moisture is contained in the living body, and moisture contained in the living body may not be accurately measured. For example, when the penetration depth of the current applied to the living body is small, even if moisture is stored in the lung due to pulmonary edema or the like, it may not be possible to measure the impedance of a storage position of the moisture. In such a case, it is not possible to accurately diagnose a state of the living body.

An object of the present disclosure is to provide a mounting tool, a measurement system, and a determination method that are capable of measuring moisture contained in a living body with higher accuracy.

SUMMARY

A mounting tool according to a first aspect of the present disclosure that is capable of executing measurement processing of impedance of a living body by applying a current to the living body and that is capable of being mounted on a user, the mounting tool including: three or more electrodes; a body shape estimation unit configured to estimate a body shape of the user mounted with the mounting tool; and a control unit configured to determine a combination of electrodes to be used for measuring the impedance of the living body among the three or more electrodes based on the body shape of the user estimated by the body shape estimation unit.

In the mounting tool according to one embodiment of the present disclosure, the body shape estimation unit includes a tightening portion that tightens at least a part of the mounting tool, the mounting tool further includes a storage unit configured to store a degree of tightening performed by the tightening portion and the combination of electrodes in association with each other, and a control unit determines the combination of electrodes based on the degree of tightening performed by the tightening portion with reference to the storage unit.

In the mounting tool according to one embodiment of the present disclosure, the body shape estimation unit includes an expansion and contraction sensor configured to output an electric signal corresponding to an amount of expansion and contraction of the mounting tool, and the control unit determines the combination of electrodes based on the electric signal output from the expansion and contraction sensor.

In the mounting tool according to one embodiment of the present disclosure, five or more of the electrodes are provided, and the combination of the electrodes includes four electrodes selected from the five or more electrodes.

A measurement system according to a second aspect of the present disclosure that includes a mounting tool capable of being mounted on a user and an information processing device, and that is capable of executing measurement processing of impedance of a living body by applying a current to the living body, in which the mounting tool includes three or more electrodes, a body shape estimation unit configured to estimate a body shape of the user mounted with the mounting tool, and a communication unit configured to transmit information on the body shape of the user estimated by the body shape estimation unit to the information processing device, and the information processing device includes a control unit configured to determine a combination of electrodes to be used for measuring impedance of the living body among the three or more electrodes based on information on the body shape of the user.

A determination method according to a third aspect of the present disclosure executed by a mounting tool that is capable of executing measurement processing of impedance of a living body by applying a current to the living body, that is capable of being mounted on a user, and that includes three or more electrodes and a body shape estimation unit configured to estimate a body shape, the determination method including: estimating, by the body shape estimation unit, the body shape of the user mounted with the mounting tool, and determining a combination of electrodes to be used for measuring the impedance of the living body among the three or more electrodes based on the body shape of the user estimated by the body shape estimation unit.

According to the present disclosure, it is possible to provide a mounting tool, a measurement system, and a determination method that are capable of measuring moisture contained in a living body with higher accuracy.

BRIEF DESCRIPTION OF THE DRAWINGS

FIG. 4 is a schematic diagram showing a four-terminal method executed by the mounting tool in FIG. 1;

FIG. 6 is a functional block diagram showing a schematic configuration of a measurement system according to a second embodiment;

DETAILED DESCRIPTION

Figure 1:
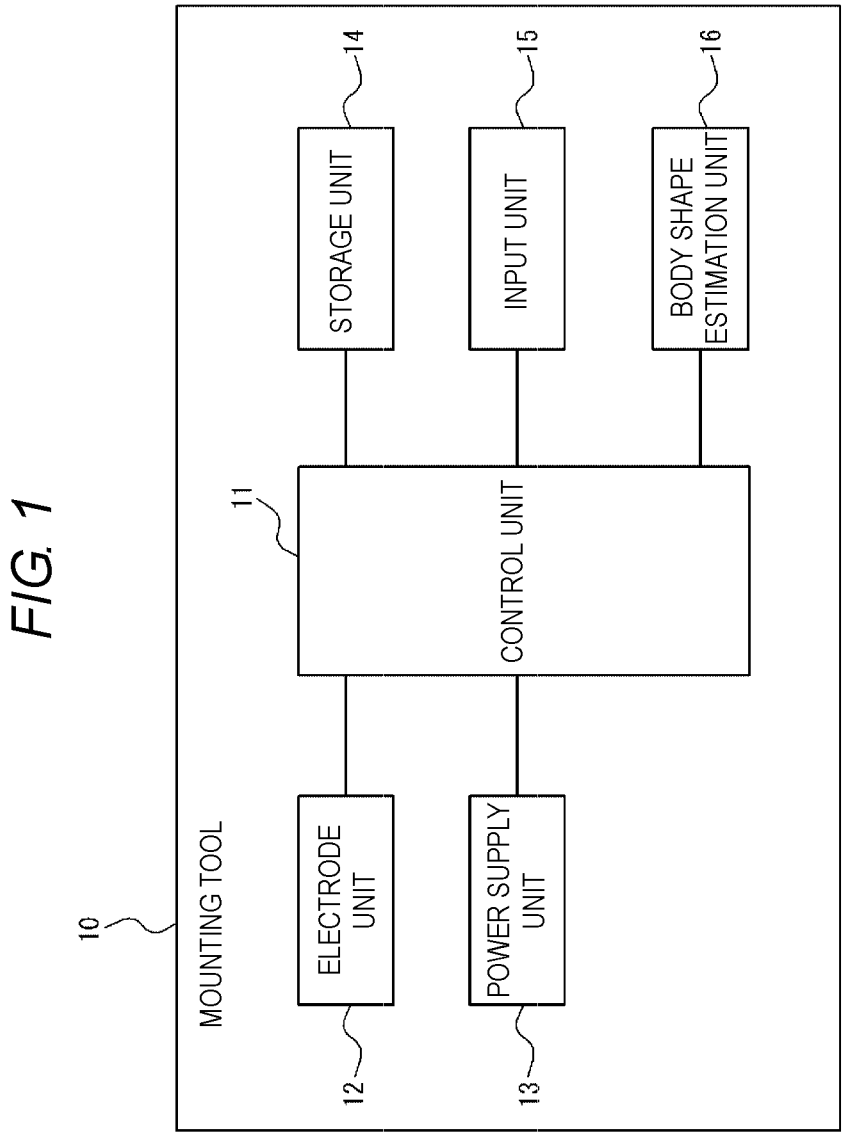
FIG. 1 is a functional block diagram showing a schematic configuration of a mounting tool according to a first embodiment.

Hereinafter, embodiments of a mounting tool, a measurement system, and a determination method according to the present disclosure will be described with reference to drawings. In the drawings, common members are denoted by the same reference numerals.

First Embodiment

FIG. 1 is a functional block diagram showing a schematic configuration of a mounting tool 10 according to a first embodiment. The mounting tool 10 is capable of measuring impedance of a living body based on a bioelectrical impedance method. That is, the mounting tool 10 can measure the impedance of a specific position of the living body by applying a current to the living body. By measuring the impedance, the mounting tool 10 can estimate a moisture amount or record a change in the moisture amount at the specific position. For example, when there is a large amount of moisture at the specific position, electricity is more likely to flow due to an influence of moisture as compared with when there is a small amount of moisture. That is, a resistance at the specific position is reduced. By using this principle, the mounting tool 10 can estimate the moisture amount or record the change in the moisture amount at the specific position.

In the present embodiment, a description will be made below assuming that the mounting tool 10 measures the impedance of a right lung of the living body serving as the specific position. By measuring the impedance of the right lung, it is possible to estimate whether moisture is stored in the right lung. The specific position is not limited to the right lung. The specific position may be a left lung. The specific position may be a site other than the lung, such as a calf. The specific position may be any site to be inspected for a moisture storage state.

As shown in FIG. 1, the mounting tool 10 includes a control unit 11, an electrode unit 12, a power supply unit 13, a storage unit 14, an input unit 15, and a body shape estimation unit 16.

The control unit 11 controls and manages the entire mounting tool 10 including functional units of the mounting tool 10. The control unit 11 includes at least one processor. The control unit 11 is a processor such as a central processing unit (CPU) that executes a program defining a control procedure or a dedicated processor specialized for processing of each function.

The control unit 11 controls an application of a current from the electrode unit 12 to the living body. The control unit 11 controls measurement processing of the impedance of the living body based on the bioelectrical impedance method. Before executing the measurement processing of the impedance of the living body, the control unit 11 determines a combination of electrodes to be used for the measurement processing of the impedance of the living body among the plurality of electrodes constituting the electrode unit 12. Details of combination determination processing executed by the control unit 11 will be described later.

The electrode unit 12 includes a plurality of electrodes. The number of electrodes provided in the electrode unit 12 may be appropriately determined according to a method of measuring the impedance performed by the mounting tool 10 or the like. In the present embodiment, the control unit 11 measures the impedance using a combination of electrodes constituted by some of the electrodes constituting the electrode unit 12. Therefore, the electrode unit 12 includes electrodes whose number is larger than the number of the electrodes used in the measurement processing of the impedance. In the present embodiment, as will be described later, the impedance is measured based on a four-terminal method. Therefore, four terminals are used to measure the impedance. Therefore, in the present embodiment, the electrode unit 12 includes five or more electrodes.

Figure 2:
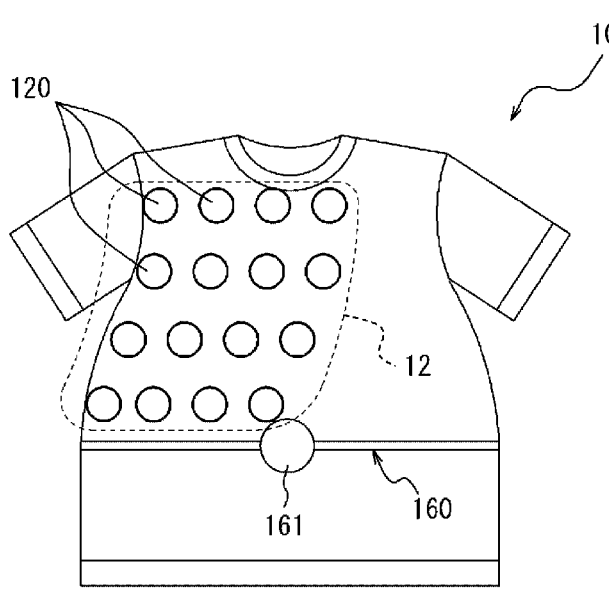
FIG. 2 is a schematic view showing an example of an arrangement of electrodes in the mounting tool in FIG. 1.

The electrodes constituting the electrode unit 12 are disposed on the mounting tool 10. FIG. 2 is a schematic view showing an example of an arrangement of electrodes in the mounting tool 10. FIG. 2 shows an example in which the mounting tool 10 is a T-shirt. In the example shown in FIG. 2, 16 electrodes 120 are disposed on the T-shirt. The 16 electrodes 120 are arranged in four horizontal rows at positions where the electrodes 120 are in contact with the right chest of the user when the user wears the T-shirt. In each row, four electrodes 120 are arranged at equal intervals. In the present embodiment, a description will be made below assuming that the electrode unit 12 includes 16 electrodes 120 and the electrodes 120 are arranged as shown in FIG. 2. With such an arrangement of the electrodes 120, when the user wears the T-shirt, the electrodes 120 come into contact with the right chest of the user, which is in the vicinity of the right lung of the user.

The power supply unit 13 is a battery that supplies power to the functional units of the mounting tool 10. The power supply unit 13 supplies power when, for example, a current is applied to the living body from the electrode unit 12.

The storage unit 14 can be a semiconductor memory, a magnetic memory, or the like. The storage unit 14 stores, for example, various types of information, a program for operating the mounting tool 10, and the like. The storage unit 14 may also function as a work memory. The storage unit 14 stores, for example, a body shape of the user estimated by the body shape estimation unit 16, which will be described later, and a combination of electrodes used for measuring the impedance of the living body in association with each other. When the control unit 11 determines the combination of the electrodes by the combination determination processing of the electrodes, the storage unit 14 stores the determined combination of the electrodes. The determined combination of electrodes is, in other words, a combination of electrodes used in the measurement processing of the impedance of the living body.

The input unit 15 receives an operation input from a user, and includes, for example, operation buttons. The input unit 15 may be, for example, a touch screen, and may display an input region for receiving an operation input from the user on a part of a display device and receive a touch operation input by the user. The user can start the measurement of the impedance by the mounting tool 10 by, for example, performing a predetermined operation input to the input unit 15.

The body shape estimation unit 16 estimates the body shape of the user mounted with the mounting tool 10. The body shape estimation unit 16 may have any configuration capable of estimating the body shape of the user mounted with the mounting tool 10.

In the present embodiment, as shown in FIG. 2, the body shape estimation unit 16 includes a tightening portion 160. As shown in FIG. 2, the tightening portion 160 is provided on the mounting tool 10. The tightening portion 160 can tighten at least a part of the mounting tool 10. In the example shown in FIG. 2, the tightening portion 160 is provided along a lateral direction of the T-shirt that is the mounting tool 10, that is, in parallel to the row in which the electrode 120 is disposed. In the example shown in FIG. 2, the tightening portion 160 is disposed in the vicinity of the lowermost row, that is, the row closest to a hem, and below the row, that is, on a hem side, among the electrodes 120 disposed in the four horizontal rows.

The tightening portion 160 has, for example, a wire therein. The tightening portion 160 includes, for example, a winding holder 161 capable of winding a wire. The winding holder 161 can wind the wire by a user operating the winding holder 161 in a state in which the user is mounted with the mounting tool 10. The winding holder 161 winds the wire, so that the mounting tool 10 is tightened to the user. At this time, the mounting tool 10 is tightened in accordance with the body shape of the user. In the example shown in FIG. 2, the winding holder 161 can be tightened in the lateral direction of the T-shirt, that is, in the direction along the waist of the user, by winding the wire. When the mounting tool 10 is tightened to the user, the mounting tool 10 is deformed into a shape conforming to the body shape of the user.

Figure 3:
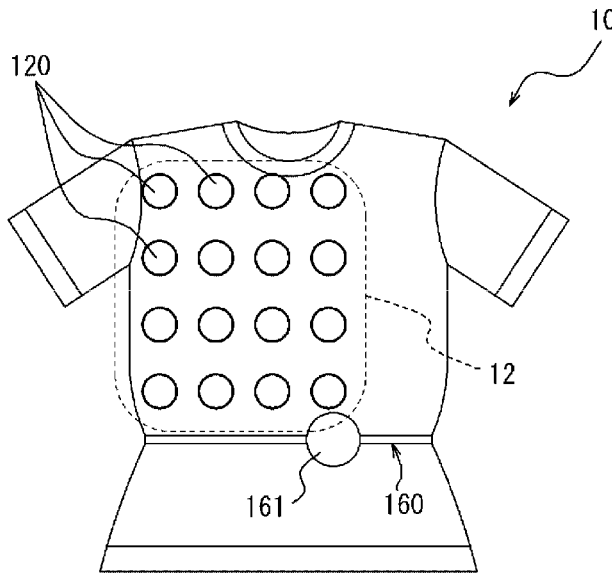
FIG. 3 is a schematic view showing a state in which the mounting tool in FIG. 2 is tightened by a tightening portion.

FIG. 3 is a schematic view showing a state in which the mounting tool 10 in FIG. 2 is tightened by the tightening portion 160. As shown in FIG. 3, when the mounting tool 10 is tightened by the tightening portion 160, a position of the T-shirt serving as the mounting tool 10 where the tightening portion 160 is provided is brought into close contact with the user. Accordingly, the entire T-shirt serving as the mounting tool 10 is deformed, and a shape of the T-shirt is changed in accordance with the body shape of the user. In the example shown in FIG. 3, in particular, in the T-shirt, a shape of an upper side (that is, a side opposite to the hem) with respect to the position where the tightening portion 160 is provided changes in a manner of approaching the user in accordance with the body shape. This makes it easier for the electrode 120 to come into contact with or come into close contact with the user mounted with the mounting tool 10.

The winding holder 161 includes a mechanism that measures a winding amount (length) of the wire. The winding holder 161 can measure a degree of tightening based on the winding amount of the wire. The degree of tightening is expressed as, for example, a numerical value. The winding amount of the wire may be used as it is as a numerical value indicating the degree of tightening. The degree of tightening can be used as a numerical value indicating the body shape of the user estimated by the body shape estimation unit 16. That is, since the shape of the mounting tool 10 changes in accordance with the body shape of the user by tightening, the body shape of the user mounted with the mounting tool 10 can be estimated based on deformation of the shape of the mounting tool 10 according to the degree of tightening. The body shape estimation unit 16 transmits, for example, a numerical value indicating the degree of tightening measured by the winding holder 161 to the control unit 11. Accordingly, the control unit 11 can acquire a numerical value related to the degree of tightening as information related to the body shape of the user.

The control unit 11 determines a combination of electrodes to be used for measuring the impedance of the living body among the plurality of electrodes 120 based on the body shape of the user estimated by the body shape estimation unit 16. Here, in the present embodiment, the body shape of the user estimated by the body shape estimation unit 16 is represented by a numerical value indicating the degree of tightening as described above. The numerical value indicating the degree of tightening changes according to the degree of deformation of the mounting tool 10. Therefore, the degree of deformation of the mounting tool 10 is estimated based on the numerical value indicating the degree of tightening, and as a result, positions where the electrodes 120 disposed on the mounting tool 10 in a deformed state are in contact with the user mounted with the mounting tool 10 are estimated.

For example, as shown in FIG. 3, when the mounting tool 10 is tightened by the tightening portion 160, the degree of deformation of the mounting tool 10 is estimated based on the degree of tightening. Based on the degree of deformation of the mounting tool 10, it is estimated which position of the user each of the electrodes 120 is in contact with.

As described above, the control unit 11 determines one combination of electrodes to be used for measuring the impedance of the living body based on the positions of the electrodes 120 in contact with the user. Specifically, the control unit 11 preferably determines one combination most suitable for the measurement processing of the impedance of the living body as a combination of electrodes to be used for measuring the impedance of the living body. That is, the control unit 11 determines, based on the estimated positions of the electrodes 120, one combination most suitable for the measurement processing of the impedance of the living body as the combination of the electrodes to be used for measuring the impedance of the living body. One combination most suitable for the measurement processing of the impedance of the living body is, for example, a combination in which the penetration depth of the current applied to the living body is most likely to be larger than a predetermined depth.

Specifically, the control unit 11 can determine the combination of electrodes to be used for measuring the impedance of the living body based on, for example, information stored in the storage unit 14. In the storage unit 14, for example, information (data table) is stored in advance in which the degree of tightening performed by the tightening portion 160, which is information on the estimated body shape of the user, and one combination most suitable for the measurement processing of the impedance of the living body according to the degree of tightening are associated with each other. The information is constructed, for example, based on the relationship between the arrangement of the electrodes 120 and the penetration depth of the current, which is performed for a sufficient number of subjects in advance. The control unit 11 determines one combination of electrodes to be used for measuring the impedance of the living body with reference to the information stored in the storage unit 14 based on the numerical value indicating the degree of tightening.

Here, the processing executed by the mounting tool 10 according to the present embodiment will be described. In the present embodiment, the mounting tool 10 measures the impedance based on a method called a four-terminal method.

Figure 4:
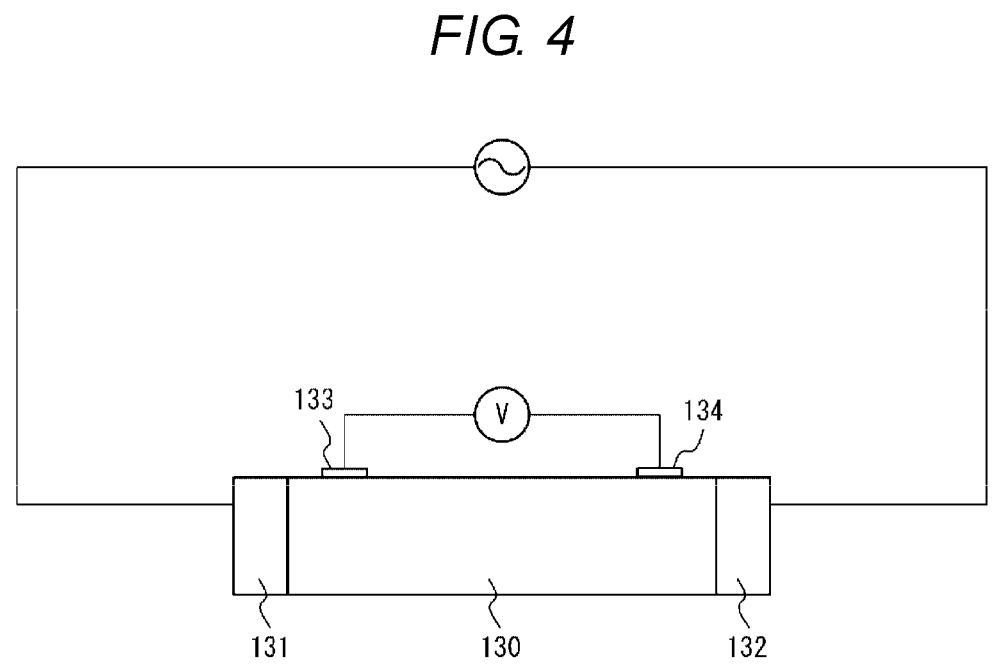

FIG. 4 is a schematic diagram showing the four-terminal method. In the four-terminal method, four terminals (electrodes) are connected to an impedance measurement target 130. Specifically, a first set of terminals including a first terminal 131 and a second terminal 132 are connected to both ends of the measurement target 130, and a current is applied to the measurement target 130 by the first set of terminals. Between the first set of terminals, a second set of terminals including a third terminal 133 and a fourth terminal 134 are connected to the measurement target 130, and a voltage between the second set of terminals is measured by the second set of terminals. Impedance between the second set of terminals can be calculated based on a current applied to the measurement target 130 by the first set of terminals and a voltage measured by the second set of terminals. Here, in the four-terminal method, since the current is negligibly small at a connection position of the third terminal 133 and the fourth terminal 134 with the measurement target 130, an electrode resistance of the third terminal 133 and the fourth terminal 134 can be ignored. Therefore, according to the four-terminal method, the impedance can be measured with high accuracy.

The mounting tool 10 measures the impedance of the right lung using the four-terminal method. Here, when the impedance of the living body is measured, a penetration depth of the current applied to the living body varies depending on a connection position of the four electrodes to the living body.

In view of this, the mounting tool 10 according to the present embodiment executes processing of determining a combination of the electrodes 120 used in the measurement processing of the impedance of the living body before executing the measurement processing of the impedance of the living body.

Figure 5:
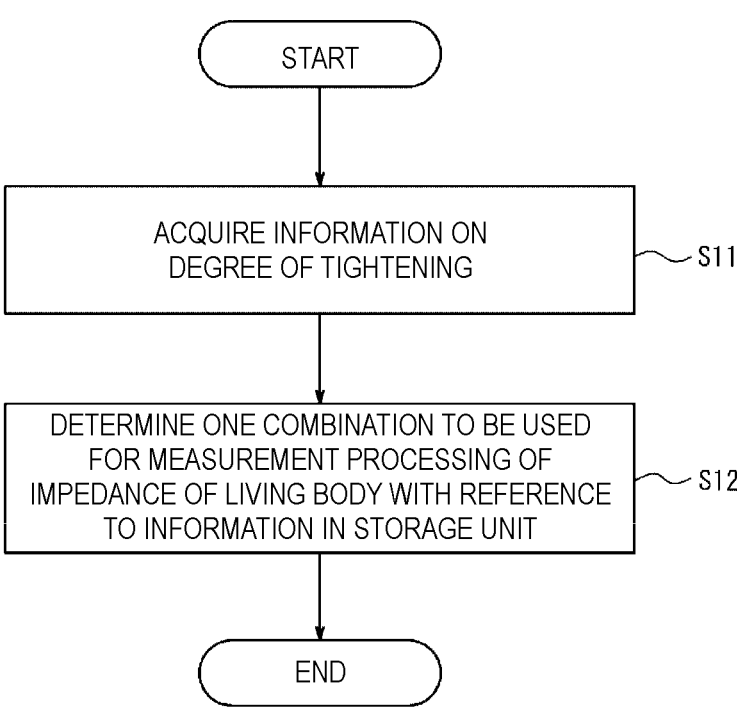
FIG. 5 is a flowchart showing an example of processing executed by a control unit in FIG. 1.

Next, details of the processing executed by the mounting tool 10 will be described with reference to FIG. 5. FIG. 5 is a flowchart showing an example of processing executed by the control unit 11 of the mounting tool 10, and is a flowchart relating to the processing of determining a combination of electrodes to be used for the measurement of the impedance of the living body. The mounting tool 10 starts the flow in FIG. 5 in a state in which the mounting tool 10 is tightened by, for example, the user mounting the mounting tool 10 and operating the winding holder 161.

First, the control unit 11 acquires information on the body shape of the user estimated by the body shape estimation unit 16. In the present embodiment, the control unit 11 acquires the information on the degree of tightening performed by the tightening portion 160 as the information on the body shape of the user estimated by the body shape estimation unit 16 (step S11).

Then, the control unit 11 determines one combination of the electrodes to be used for measuring the impedance of the living body based on the information on the degree of tightening acquired in step S11 with reference to the information stored in the storage unit 14 (step S12).

In this manner, the control unit 11 determines one combination to be used for the measurement processing of the impedance of the living body, and then executes the measurement processing of the impedance of the living body using the electrode 120 of the determined combination.

As described above, according to the mounting tool 10 in the present embodiment, the control unit 11 determines the combination of the electrodes to be used for measuring the impedance of the living body based on the information on the body shape of the user estimated by the body shape estimation unit 16, that is, the information on the degree of tightening performed by the tightening portion 160. Therefore, according to the mounting tool 10 in the present embodiment, the electrodes 120 suitable for the measurement processing of the impedance of the living body can be selected as the combination of the electrodes to be used for measuring the impedance of the living body among the plurality of electrodes 120 in contact with the user in accordance with the body shape of the user indicated by the degree of tightening. Accordingly, according to the mounting tool 10 in the present embodiment, the moisture contained in the living body can be measured with higher accuracy.

According to the mounting tool 10 in the present embodiment, the body shape estimation unit 16 includes the tightening portion 160, and the storage unit 14 stores the degree of tightening performed by the tightening portion 160 and a combination of electrodes according to the degree of tightening in association with each other. The control unit 11 determines a combination of electrodes based on the degree of tightening performed by the tightening portion 160 with reference to the storage unit 14. Accordingly, the mounting tool 10 can select the combination of electrodes to be used for measuring the impedance of the living body in accordance with the body shape of the user based on the degree of tightening performed by the tightening portion 160. Accordingly, according to the mounting tool 10 in the present embodiment, the moisture contained in the living body can be measured with higher accuracy.

The mounting tool 10 according to the present embodiment includes five or more electrodes 120, and the combination of the electrodes 120 includes four electrodes selected from the five or more electrodes 120. Accordingly, the mounting tool 10 according to the present embodiment can be formed as a device that measures the impedance based on the four-terminal method.

In the present embodiment, it has been described that the tightening portion 160 is provided along a lateral direction of the T-shirt which is the mounting tool 10. However, the tightening portion 160 may be provided along another direction. For example, the tightening portion 160 may be provided along a longitudinal direction of the T-shirt, that is, parallel to the column in which the electrodes 120 are arranged. The tightening portion 160 may be provided in a direction other than the lateral direction and the longitudinal direction. The tightening portion 160 may be provided in a plurality of directions such as the lateral direction and the longitudinal direction.

In the present embodiment, it has been described that the tightening portion 160 is disposed in the vicinity of the row closest to the hem and closer to the hem side with respect to the row among the electrodes 120 disposed in the four horizontal rows. However, the position where the tightening portion 160 is disposed is not limited to this position. The tightening portion 160 may be provided at another position. The tightening portion 160 may be provided at a position where at least a part of the mounting tool 10 can be tightened.

A plurality of tightening portions 160 may be provided. For example, in a T-shirt that is the mounting tool 10, the plurality of tightening portions 160 may be provided at different heights in the lateral direction, that is, at positions where distances from the hem are different. In this case, since the mounting tool 10 can be tightened at a plurality of different positions of the user, the body shape of the user can be estimated more accurately.

Second Embodiment

In the first embodiment, an example has been described in which the present disclosure is implemented as the mounting tool 10. However, the present disclosure is not necessarily implemented only by the mounting tool 10. For example, the present disclosure may be implemented as a measurement system including the mounting tool 10 and other devices. An example in which the present disclosure is implemented as the measurement system will be described as a second embodiment.

FIG. 6 is a functional block diagram showing a schematic configuration of a measurement system 20 according to the second embodiment. The measurement system 20 includes a mounting tool 30 and an information processing device 40. The mounting tool 30 and the information processing device 40 are connected to each other through wired communication or wireless communication so as to execute information communication with each other. The measurement system 20 achieves the function of the mounting tool 10 according to the first embodiment by the mounting tool 30 and the information processing device 40. Hereinafter, description of similar points as those according to the first embodiment will be appropriately omitted, and different points will be mainly described.

The mounting tool 30 is capable of measuring impedance of a living body based on the bioelectrical impedance method. As shown in FIG. 6, the mounting tool 30 includes a control unit 31, an electrode unit 32, a power supply unit 33, a storage unit 34, an input unit 35, a body shape estimation unit 36, and a communication unit 37.

In the mounting tool 30 according to the present embodiment, configurations and functions of the electrode unit 32, the power supply unit 33, the storage unit 34, the input unit 35 and the body shape estimation unit 36 may be similar as the configurations and functions of the electrode unit 12, the power supply unit 13, the storage unit 14, the input unit 15 and the body shape estimation unit 16 of the mounting tool 10 according to the first embodiment, and thus the description thereof will be omitted here.

In the mounting tool 30, the control unit 31 controls and manages the entire mounting tool 30 including functional units of the mounting tool 30. In the present embodiment, the control unit 31 controls the application of a current from the electrode unit 32 to the living body based on a control signal received from the information processing device 40. The control unit 31 transmits information on a body shape of a user estimated by the body shape estimation unit 16 to the information processing device 40 via the communication unit 37.

The communication unit 37 transmits and receives various types of information by executing wired communication or wireless communication with the information processing device 40. For example, the communication unit 37 receives, from the information processing device 40, a control signal that causes an application of the current to the living body. For example, the communication unit 37 transmits information on the body shape of the user estimated by the body shape estimation unit 36 of the mounting tool 30 to the information processing device 40.

The information processing device 40 is, for example, an electronic device such as a computer device or a terminal device. The information processing device 40 controls the application of current to the living body in the mounting tool 30, and executes various types of information processing based on the information received from the mounting tool 30. The information processing device 40 determines, for example, a combination of electrodes to be used for the measurement processing of the impedance of the living body among the plurality of electrodes constituting the electrode unit 32 of the mounting tool 30. In the information processing device 40, for example, an application for executing processing of determining the combination of electrodes used for the measurement processing of the impedance of the living body may be installed in advance.

For example, as shown in FIG. 6, the information processing device 40 includes a control unit 41, a storage unit 44, an input unit 45, a display unit 46, and a communication unit 47.

The control unit 41 controls and manages the entire information processing device 40 including the functional units of the information processing device 40. The control unit 41 includes at least one processor. The control unit 41 is a processor such as the CPU that executes the program defining a control procedure or a dedicated processor specialized for processing of each function.

The control unit 41 generates a control signal for causing the mounting tool 30 to apply a current to the living body, and transmits the control signal to the mounting tool 30 via the communication unit 47. Before executing the measurement processing of the impedance of the living body by the mounting tool 30, the control unit 41 determines a combination of electrodes to be used for the measurement processing of the impedance of the living body among the plurality of electrodes constituting the electrode unit 32 based on the information received from the mounting tool 30. A method of determination may be similar as the method executed by the mounting tool 10 according to the first embodiment.

The storage unit 44 can be a semiconductor memory, a magnetic memory, or the like. The storage unit 44 stores, for example, various types of information, a program for operating the information processing device 40, and the like. The storage unit 44 may also function as a work memory. The storage unit 44 stores, for example, the body shape of the user estimated by the body shape estimation unit 36, and the combination of electrodes to be used for measuring the impedance of the living body in association with each other. For example, when the control unit 41 determines the combination of the electrodes by the determination processing of the combination of the electrodes, the storage unit 44 stores the determined combination of the electrodes.

The input unit 45 receives an operation input from the user, and includes, for example, operation buttons. The input unit 45 is, for example, a touch screen, and may display an input region for receiving an operation input from the user on a part of the display device and receive a touch operation input by the user. The user can start the control by the information processing device 40 by, for example, executing a predetermined operation input to the input unit 45 and thereby start the measurement of the impedance by the mounting tool 30.

The display unit 46 is a display device which is a well-known display such as a light emitting diode (LED) display, a liquid crystal display (LCD), or an organic electroluminescence display (OELD). The display unit 46 displays various types of information. For example, the display unit 46 displays that the measurement processing of the impedance of the living body is being executed. Accordingly, the user who views the display can know that the measurement processing of the impedance of the living body is being executed.

The communication unit 47 transmits and receives various types of information by executing wired communication or wireless communication with the mounting tool 30. For example, the communication unit 47 transmits the control signal that causes the mounting tool 30 to apply the current to the living body. For example, the communication unit 47 receives, from the mounting tool 30, information on the body shape of the user estimated by the body shape estimation unit 36.

Figure 7:
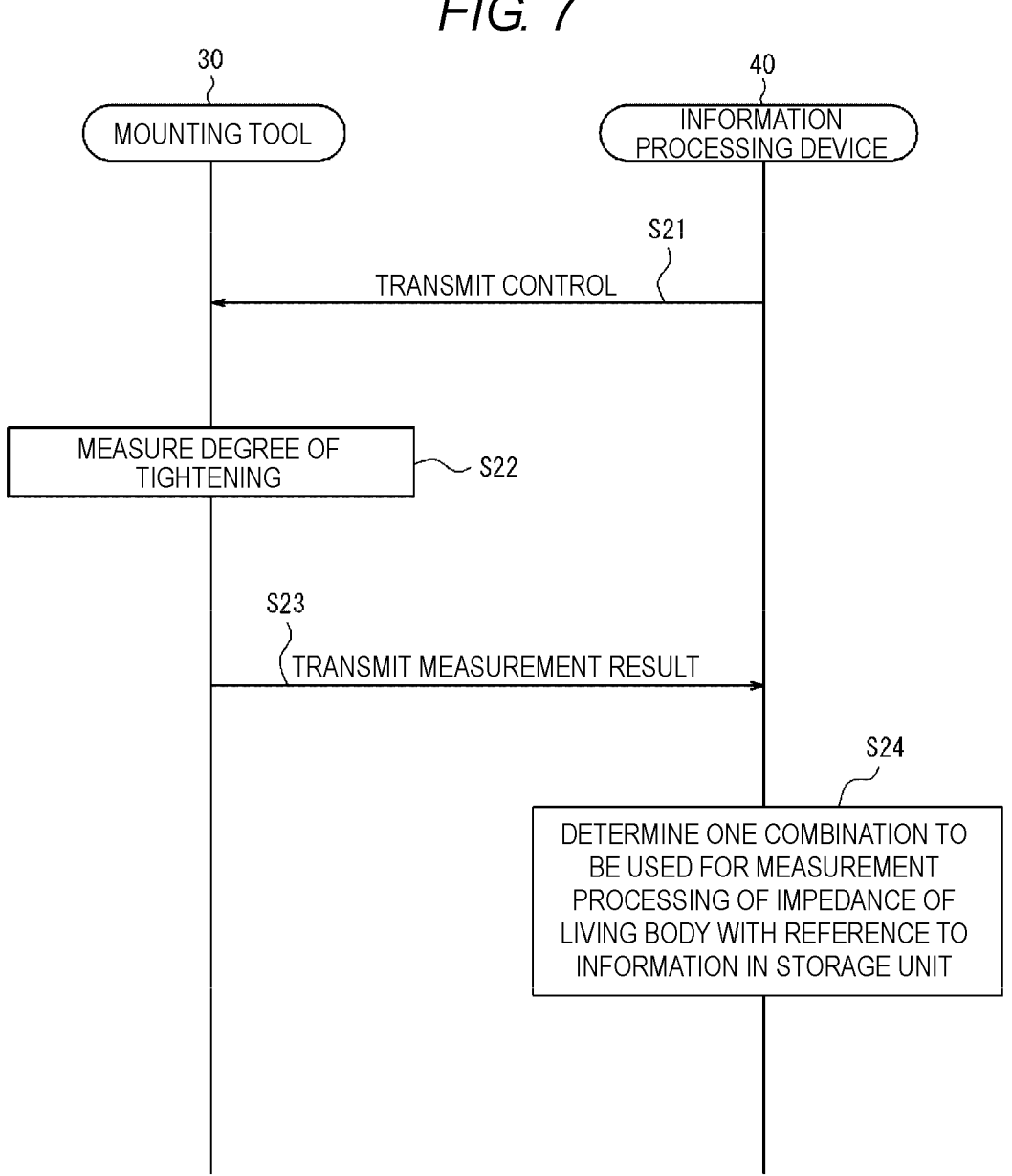
FIG. 7 is a sequence diagram showing an example of processing executed by the measurement system in FIG. 6.

Here, details of the processing executed by the measurement system 20 will be described with reference to FIG. 7. FIG. 7 is a sequence diagram showing an example of a processing performed by the measurement system 20 in FIG. 6, and is a sequence diagram related to processing of determining a combination of electrodes to be used for measuring the impedance of the living body. A sequence in FIG. 7 starts in a state in which the mounting tool 30 is tightened by, for example, the user mounting the mounting tool 30 and operating the winding holder 161.

In the processing of determining the combination of the electrodes to be used for measuring the impedance of the living body, first, the information processing device 40 transmits the control signal for executing estimation processing of the body shape of the user to the mounting tool 30 (step S21).

When receiving the control signal from the information processing device 40, the mounting tool 30 measures the degree of tightening of the mounting tool 30 performed by the tightening portion 160 provided in the body shape estimation unit 36 as information on the body shape of the user (step S22).

Next, the mounting tool 30 transmits a measurement result of the degree of tightening in step S22 to the information processing device 40 (step S23).

When a result of the measurement of the degree of tightening executed by the mounting tool 30 is received, the information processing device 40 determines one combination of the electrodes to be used for measuring the impedance of the living body based on the information on the degree of tightening acquired in step S23 with reference to the information stored in the storage unit 44 (step S24). The specific processing in step S24 may be similar as that in step S12 in FIG. 4. In this manner, the information processing device 40 determines one combination to be used for the measurement processing of the impedance of the living body, and then executes the measurement processing of the impedance of the living body using the electrode 120 of the determined combination.

As described above, according to the measurement system 20 in the present embodiment, the combination of the electrodes to be used for measuring the impedance of the living body is selected in accordance with the body shape of the user. Therefore, according to the measurement system 20, the moisture contained in the living body can be measured with higher accuracy.

In the second embodiment, an example has been described in which the mounting tool 30 provides the information on the degree of tightening as the information on the body shape of the user to the information processing device 40 via the communication unit 37. However, the information on the degree of tightening may not necessarily be provided to the information processing device 40 via the communication unit 37.

Figure 8:
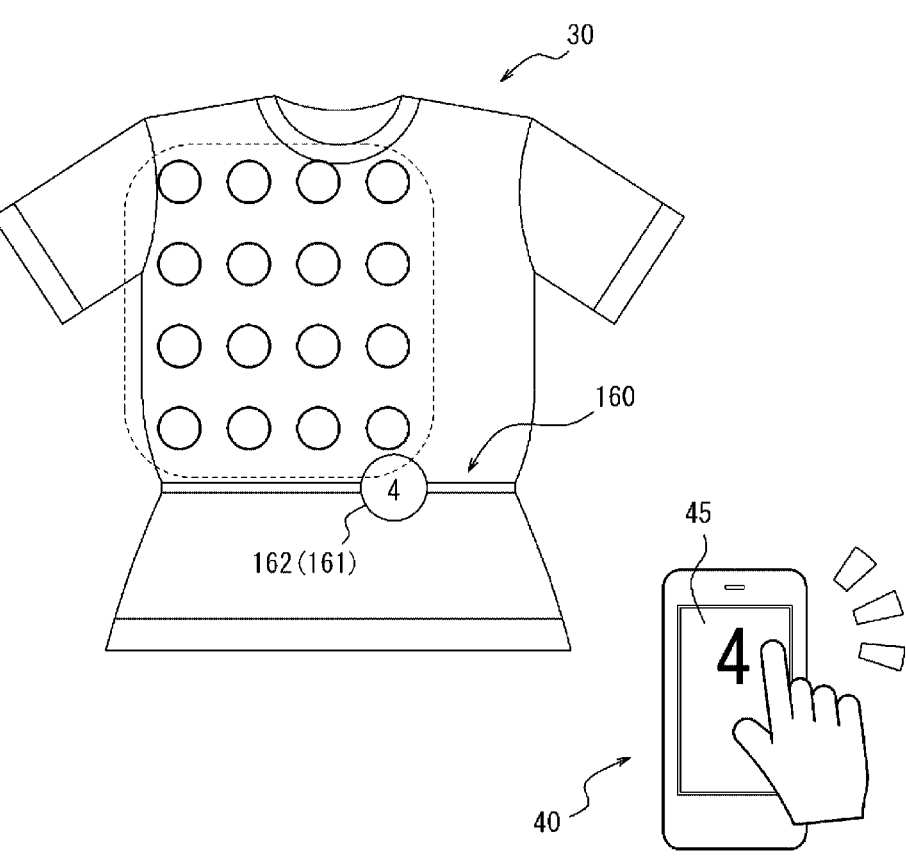
FIG. 8 is a schematic diagram showing an aspect of use of a measurement system according to a modification.

For example, the information on the degree of tightening may be provided to the information processing device 40 by the user operating the input unit 45. In this case, for example, as schematically shown in FIG. 8, the tightening portion 160 includes a display unit 162 that displays a numerical value indicating the degree of tightening. The display unit 162 that displays the numerical value indicating the degree of tightening is, for example, a dial in which the numerical value is displayed according to the winding amount of the winding holder 161.

In this case, the user checks the numerical value indicated by the dial in a state in which the mounting tool 10 is tightened by attaching the mounting tool 10 and operating the winding holder 161. As shown in FIG. 8, the user inputs the read numerical value to the input unit 45 of the information processing device 40. Accordingly, the information processing device 40 can acquire a numerical value as information indicating the degree of tightening. Similar as in step S24 of the flow in FIG. 7, the information processing device 40 determines one combination of the electrodes to be used for measuring the impedance of the living body based on the acquired information on the degree of tightening with reference to the information stored in the storage unit 44.

As described above, also in a case in which information on the degree of tightening is input by the user, the combination of the electrodes to be used for measuring the impedance of the living body is selected in accordance with the body shape of the user. Therefore, according to the measurement system 20, the moisture contained in the living body can be measured with higher accuracy.

Third Embodiment

In the first embodiment described above, a case has been described in which the body shape estimation unit 16 includes the tightening portion 160. However, the body shape estimation unit 16 may not necessarily include the tightening portion 160. The body shape estimation unit 16 may have a configuration capable of estimating the body shape of the user mounted with the mounting tool 10. Here, as a third embodiment, an example will be described in which the body shape estimation unit 16 includes an expansion and contraction sensor that measures an amount of expansion and contraction. In the third embodiment, the functional blocks provided in the mounting tool 10 may be similar as those provided in the mounting tool 10 according to the first embodiment. Here, a description will be made below assuming that the mounting tool 10 according to the third embodiment includes the functional blocks similar to those of the mounting tool 10 according to the first embodiment.

In the third embodiment, the mounting tool 10 is formed as an elastic wear of a free size. Specifically, the mounting tool 10 includes a material having high elasticity, such as polyurethane. When the user is mounted with the mounting tool 10, the mounting tool 10 expands and contracts in accordance with the body shape of the user and deforms.

The mounting tool 10 includes the expansion and contraction sensor that measures the amount of expansion and contraction as the body shape estimation unit 16. The expansion and contraction sensor is provided at a position in the mounting tool 10. At the position, the amount of expansion and contraction of at least a position where the electrode 120 is disposed can be measured. A plurality of expansion and contraction sensors may be disposed at appropriate positions in the mounting tool 10.

The expansion and contraction sensor may be any known sensor that measures the amount of expansion and contraction. For example, the expansion and contraction sensor is a sensor in which an electric resistance changes according to the amount of expansion and contraction and the change in the electric resistance is used as a sensor function to measure the amount of expansion and contraction.

When the user is mounted with the mounting tool 10, the expansion and contraction sensor expands as the mounting tool 10 deforms in accordance with the body shape of the user. The expansion and contraction sensor outputs, to the control unit 11, an electric signal corresponding to the amount of expansion and contraction. Accordingly, the expansion and contraction sensor can transmit an electric signal of the result of the measurement of the amount of expansion and contraction as the information on the body shape of the user to the control unit 11. In the present embodiment, the degree of deformation of the mounting tool 10 is estimated based on the electric signal of the measurement result of the amount of expansion and contraction of the expansion and contraction sensor, and as a result, positions where the electrodes 120 disposed on the mounting tool 10 in a deformed state are in contact with the user mounted with the mounting tool 10 are estimated.

Similar as in the first embodiment, the storage unit 14 stores the body shape of the user estimated by the body shape estimation unit 16, which will be described later, and a combination of electrodes to be used for measuring the impedance of the living body in association with each other. Specifically, in the present embodiment, the storage unit 14 stores the electrical signal of the measurement result of the amount of expansion and contraction as the information on the body shape of the user, which is received from each expansion and contraction sensor, and the combination of the electrodes to be used for measuring the impedance of the living body in association with each other.

When the control unit 11 receives the electric signal of the measurement result of the amount of expansion and contraction from the expansion and contraction sensor constituting the body shape estimation unit 16, the control unit 11 determines one combination of electrodes to be used for measuring the impedance of the living body according to the electric signal of the measurement result of the amount of expansion and contraction with reference to the information stored in the storage unit 14. In this manner, the control unit 11 determines one combination to be used for the measurement processing of the impedance of the living body, and then executes the measurement processing of the impedance of the living body using the electrode 120 of the determined combination.

As described above, according to the mounting tool 10 in the third embodiment, the combination of the electrodes to be used for measuring the impedance of the living body is selected in accordance with the body shape of the user. Therefore, the moisture contained in the living body can be measured with higher accuracy. According to the mounting tool 10 in the third embodiment, since the body shape estimation unit 16 can estimate the body shape of the user only by the user being mounted with the mounting tool 10, the user does not need to perform any operation on the mounting tool 10 in order to determine one combination of the electrodes to be used for measuring the impedance of the living body. Therefore, the mounting tool 10 is highly convenient for the user.

In the above embodiment, a case has been described in which the impedance is measured based on the four-terminal method. However, the present disclosure is also applicable to a case in which the impedance is measured based on a method other than the four-terminal method, for example, a two-terminal method.

When the impedance is measured based on the two-terminal method, two terminals are used for the measurement of the impedance. Therefore, is this case, the electrode unit 12 may include three or more electrodes. In this case, the combination of the electrodes to be used for the measurement processing of the impedance of the living body includes two electrodes selected from three or more electrodes. In the case of the two-terminal method, the impedance can be measured with a smaller number of terminals.

In the above embodiment, it has been described that the electrode unit 12 is constituted by the 16 electrodes 120. However, the number of the electrodes 120 provided in the electrode unit 12 is not limited thereto. The electrode unit 12 may include an appropriate number of electrodes 120 according to a specification of the mounting tool 10 or the like. As the number of the electrodes 120 provided in the electrode unit 12 increases, the number of candidates for the combination of the terminals used in the measurement processing of the impedance of the living body increases. Therefore, as the number of the electrodes 120 provided in the electrode unit 12 increases, the chance of occurrence of a combination in which the penetration depth of the current is larger is higher.

In the above present embodiment, it has been described that the 16 electrodes 120 are arranged at equal intervals in four rows. However, the arrangement of the electrodes 120 is not limited thereto. The electrode 120 may be appropriately disposed in the mounting tool.

The body shape estimation unit is not limited to that described in the above embodiment. The body shape estimation unit may be any mechanism capable of estimating the body shape of the user mounted with the mounting tool.

In the above embodiment, it has been described that the mounting tool 10 is the T-shirt and the impedance of the right lung of the living body is measured. However, the present disclosure is not limited to this aspect. As the mounting tool, an appropriate one may be used according to a position where the impedance is measured in the living body. For example, when the impedance of the calf of the living body is measured, the mounting tool may be implemented as a mounting tool to be mounted on the lower body, such as trousers or tights.

It is preferable that the mounting tool is formed of a material and in a form that are easily brought into close contact with the living body. Since the mounting tool is formed of a material and in a form that are easily brought into close contact with the living body, the electrode 120 disposed on the mounting tool is easily brought into contact with the living body.

The mounting tool, the measurement system, and the determination method according to the present disclosure are not limited to the configurations specified in the embodiments described above, and various modifications can be made without departing from the gist of the invention described in the claims. For example, functions and the like in the components, the steps, and the like can be rearranged in a manner of not being logically contradictory, and a plurality of components, steps, and the like can be combined into one or divided.

INDUSTRIAL APPLICABILITY

The present disclosure relates to a mounting tool, a measurement system, and a determination method. The mounting tool, the measurement system, and the determination method according to the present disclosure can be applied to, for example, a patient of pulmonary edema. According to the mounting tool, the measurement system, and the determination method in the present disclosure, it is possible to measure the storage state of moisture in the patient of pulmonary edema with higher accuracy.

What is claimed is:

1. A mounting tool that is capable of executing measurement processing of impedance of a living body by applying a current to the living body and that is capable of being mounted on a user, the mounting tool comprising:
   three or more electrodes arranged in a two-dimensional pattern along a horizontal axis and a vertical axis;
   a body shape estimation unit configured to estimate a body shape of the user mounted with the mounting tool independently of signals from the three or more electrodes, and a control unit configured to determine a combination of electrodes to be used for measuring the impedance of the living body among the three or more electrodes based on the body shape of the user estimated by the body shape estimation unit, and to control the three or more electrodes to apply the current based on the determined combination of electrodes, wherein the combination of electrodes to be used is determined prior to executing the process of measuring the impedance.

2. The mounting tool according to claim 1, wherein:

the body shape estimation unit includes a tightening device that tightens at least a part of the mounting tool, and a storage unit configured to store a degree of tightening performed by the tightening device and the combination of electrodes in association with each other, and the control unit determines the combination of electrodes based on the degree of tightening performed by the tightening device with reference to the storage unit.

3. The mounting tool according to claim 1, wherein:

the body shape estimation unit includes an expansion and contraction sensor configured to output an electric signal corresponding to an amount of expansion and contraction of the mounting tool, and the control unit determines the combination of electrodes based on the electric signal output from the expansion and contraction sensor.

4. The mounting tool according to claim 1, comprising five or more of the electrodes, wherein the combination of the electrodes includes four electrodes selected from the five or more electrodes.

5. A measurement system that includes a mounting tool capable of being mounted on a user and an information processing device, and that is capable of executing measurement processing of impedance of a living body by applying a current to the living body, wherein the mounting tool includes;

three or more electrodes arranged in a two-dimensional pattern along a horizontal axis and a vertical axis, a body shape estimation unit configured to estimate a body shape of the user mounted with the mounting tool independently of signals from the three or more electrodes, and a communication unit configured to transmit information on the body shape of the user estimated by the body shape estimation unit to the information processing device, and the information processing device includes a control unit configured to determine a combination of electrodes to be used for measuring impedance of the living body among the three or more electrodes based on the information on the body shape of the user, and to control the three or more electrodes to apply the current based on the determined combination of electrodes, wherein the combination of electrodes to be used is determined prior to executing the process of measuring the impedance.

6. The measurement system according to claim 5, wherein:

the body shape estimation unit includes a tightening device that tightens at least a part of the mounting tool, and a storage unit configured to store a degree of tightening performed by the tightening device and the combination of electrodes in association with each other, and the control unit determines the combination of electrodes based on the degree of tightening performed by the tightening device with reference to the storage unit.

7. The measurement system according to claim 5, wherein:

the body shape estimation unit includes an expansion and contraction sensor configured to output an electric signal corresponding to an amount of expansion and contraction of the mounting tool, and the control unit determines the combination of electrodes based on the electric signal output from the expansion and contraction sensor.

8. The measurement system according to claim 5, wherein the mounting tool comprises five or more of the electrodes, and the combination of the electrodes includes four electrodes selected from the five or more electrodes.

9. A determination method executed by a mounting tool that is capable of executing measurement processing of impedance of a living body by applying a current to the living body, that is capable of being mounted on a user, and that includes three or more electrodes arranged in a two-dimensional pattern along a horizontal axis and a vertical axis, and a body shape estimation unit configured to estimate a body shape independently of signals from the three or more electrodes, the determination method comprising:

estimating, by the body shape estimation unit, the body shape of the user mounted with the mounting tool independently of signals from the three or more electrodes, determining a combination of electrodes to be used for measuring the impedance of the living body among the three or more electrodes based on the body shape of the user estimated by the shape estimation unit, and controlling the three or more electrodes to apply the current based on the determined combination of electrodes, wherein the combination of electrodes to be used is determined prior to executing the process of measuring the impedance.

10. The determination method according to claim 9, wherein:

the body shape estimation unit comprises a tightening device that tightens at least a part of the mounting tool, and a storage unit configured to store a degree of tightening performed by the tightening device and the combination of electrodes in association with each other, and the combination of electrodes is determined based on the degree of tightening performed by the tightening device with reference to the storage unit.

11. The determination method according to claim 9, wherein:

the body shape estimation unit comprises an expansion and contraction sensor configured to output an electric signal corresponding to an amount of expansion and contraction of the mounting tool, and the combination of electrodes is determined based on the electric signal output from the expansion and contraction sensor.

12. The determination method according to claim 9, wherein the mounting tool comprises five or more of the electrodes, and the combination of the electrodes includes four electrodes selected from the five or more electrodes.

* * * * *